(12) United States Patent
Komsky et al.

(10) Patent No.: US 10,228,354 B2
(45) Date of Patent: Mar. 12, 2019

(54) SINGLE CHANNEL SCANNING ACOUSTIC MICROSCOPE WITH MULTIPLE FOCUSED ULTRASONIC TRANSDUCERS

(71) Applicant: Sonoscan Inc., Elk Grove Village, IL (US)

(72) Inventors: Igor N. Komsky, Long Grove, IL (US); Lawrence W. Kessler, Buffalo Grove, IL (US)

(73) Assignee: Nordson Corporation, Westlake, OH (US)

( * ) Notice: Subject to any disclaimer, the term of this patent is extended or adjusted under 35 U.S.C. 154(b) by 885 days.

(21) Appl. No.: 14/065,105

(22) Filed: Oct. 28, 2013

(65) Prior Publication Data

US 2014/0116143 A1 May 1, 2014

Related U.S. Application Data

(60) Provisional application No. 61/795,873, filed on Oct. 26, 2012.

(51) Int. Cl.
| | | |
|---|---|---|
| G01N 29/34 | (2006.01) | |
| G01N 29/06 | (2006.01) | |
| G01N 29/26 | (2006.01) | |
| G01N 29/28 | (2006.01) | |

(52) U.S. Cl.
CPC ....... *G01N 29/343* (2013.01); *G01N 29/0681* (2013.01); *G01N 29/262* (2013.01); *G01N 29/28* (2013.01); *G01N 29/34* (2013.01); *G01N 29/341* (2013.01)

(58) Field of Classification Search
CPC .... G01N 29/34; G01N 29/341; G01N 29/343; G01N 29/262; G01N 29/28; G01N 29/0681
USPC .......... 73/606, 607, 602, 625, 626, 628, 618
See application file for complete search history.

(56) References Cited

U.S. PATENT DOCUMENTS

| | | |
|---|---|---|
| 4,518,992 A | 5/1985 | Kessler et al. |
| 4,781,067 A | 11/1988 | Cichanski |
| 4,866,986 A | 9/1989 | Cichanski |
| 5,600,068 A | 2/1997 | Kessler et al. |
| 5,684,252 A | 11/1997 | Kessler et al. |
| 6,357,136 B1 | 3/2002 | Erickson et al. |
| 6,460,414 B1 | 10/2002 | Erickson et al. |
| 6,880,387 B2 | 4/2005 | Kessler et al. |
| 6,890,302 B2 | 5/2005 | Oravecz et al. |
| 6,895,820 B2 | 5/2005 | Oravecz et al. |
| 6,981,417 B1 | 1/2006 | Oravecz |
| 7,000,475 B2 | 2/2006 | Oravecz et al. |
| 7,395,713 B2 | 7/2008 | Kessler et al. |
| 7,522,780 B2 | 4/2009 | Oravecz et al. |
| 7,584,664 B2 | 9/2009 | Kessler |

(Continued)

*Primary Examiner* — Lisa M Caputo
*Assistant Examiner* — Rose M Miller
(74) *Attorney, Agent, or Firm* — Baker & Hostetler LLP

(57) ABSTRACT

A single channel scanning acoustic microscope that increases the throughput of the acoustic imaging system by connecting a multi-transducer assembly in parallel to a single channel electronic circuit. The single channel scanning acoustic microscope includes multiple transducers configured to generate a time delay for individual ultrasonic waves generated by each transducer, wherein a pulse generator simultaneously sends a pulse signal to the multi-transducer assembly.

32 Claims, 17 Drawing Sheets

(56) References Cited

U.S. PATENT DOCUMENTS

| | | | |
|---|---|---|---|
| 7,926,350 B2* | 4/2011 | Kroning | G01N 29/043 600/437 |
| 2002/0121142 A1* | 9/2002 | Bae | G01S 7/52036 73/602 |
| 2008/0110263 A1* | 5/2008 | Klessel | G01S 7/52028 73/602 |
| 2009/0095086 A1 | 4/2009 | Kessler et al. | |
| 2011/0245677 A1* | 10/2011 | Sato | A61B 8/08 600/447 |
| 2012/0125109 A1 | 5/2012 | Kessler et al. | |
| 2012/0125110 A1 | 5/2012 | Kessler et al. | |
| 2012/0259225 A1* | 10/2012 | Tashiro | A61B 8/14 600/443 |
| 2013/0060142 A1* | 3/2013 | Ishihara | A61B 8/14 600/447 |
| 2013/0150723 A1* | 6/2013 | Satoh | A61B 8/4411 600/459 |
| 2013/0165796 A1* | 6/2013 | Tashiro | A61B 8/4472 600/459 |

* cited by examiner

SINGLE CHANNEL SCANNING ACOUSTIC MICROSCOPE WITH MULTIPLE FOCUSED ULTRASONIC TRANSDUCERS

RELATED APPLICATIONS

This application claims the benefit of U.S. Provisional Application No. 61/795,873 filed Oct. 26, 2012, which is hereby incorporated by reference in its entirety.

STATEMENT REGARDING FEDERALLY SPONSORED RESEARCH AND DEVELOPMENT

N/A

BACKGROUND OF THE DISCLOSURE

Field of the Disclosure

The present invention relates to a single channel scanning acoustic microscope which uses multiple focused ultrasonic transducers.

Discussion of the Background

The effectiveness of any non-destructive inspection, evaluation methodology and acoustic imaging methodology depends particularly on the throughput of the inspection system. Referring to FIG. 1A, a prior art acoustic imaging system with a single focused transducer 1 is shown. The acoustic imaging system with a single focused transducer 1 comprises a transducer 10, a pulser 20, an amplifier 30, a digital converter 40 and a visual display, such as a monitor 50. Its throughput is largely limited by two factors. One limiting factor is the scanning speed of the X-Y driver system that moves the ultrasonic transducer with respect to the part or sample being inspected. A second limiting factor is the pulse repetition frequency (PRF) or rate that is expressed by the number of pulses that can be generated by the pulse generator-piezoelectric 20 crystal circuit in one unit of time (usually 1 second).

For modern acoustic imaging systems this number varies from 10 KHz to 25 KHz and can be translated into a 100 μsec to 40 μsec time interval between sequential pulses. This interval determines the time that is available for an ultrasonic wave generation and round-trip travel and reception at each point of the scanned area (image pixel). Increasing the PRF can result in a higher speed of the acoustic imaging and subsequently a higher throughput. Unfortunately, at high frequencies pulse generation technology is very close to the achievable limits of PRF.

A multi-transducer inspection procedure is an alternative to the single transducer high-speed scanning procedures that are rapidly approaching the physical and technological limits for speed increases. Multiple transducers 10, 11, 12 can be concurrently deployed on multiple parts or multiple areas of the same part. Multi-transducer inspection assemblies 2 are conventionally connected in one of two ways. First, the separate transducers 10, 11, 12 can be connected "in parallel" to multi-channel electronics with independent channels for the signal generation and data acquisition as shown in prior art FIG. 1B. Each independent channel comprises a pulser 21, 22, 23, an amplifier 31, 32, 33, a digital converter 41, 42, 43 and a visual display, such as a monitor 50. Second, the separate transducers 51, 52, 53 can be connected "in sequence" to a single electronic channel, comprising a pulser 24, an amplifier 34, a digital converter 44 and a visual display 50, through a multiplexing unit 60 as shown in FIG. 1C. The multiplexer selects one of several input signals from the transducer group and forwards the selected input into a single electronic channel.

Multi-channel electronics make it possible to independently maintain all inspection parameters (pulse repetition rate, speed, resolution, etc.) selected for each individual channel without interference between signals. However, the multi-channel approach is very expensive to implement in practice as it requires the deployment of multiple signal generators (i.e., the pulsers shown in FIG. 1B) as well as expensive multi-channel signal conditioning units such as the amplifiers 31, 32, 33 and A/D converters 41, 42, 43.

A single channel approach with a multiplexing unit as shown in FIG. 1 C does not result in a substantial component cost increase because the only added costs are those of the additional transducers and of the multiplexing unit. Unfortunately, this approach significantly limits the scanning speed of the inspection system. Electronic pulses are generated by a single pulse generator 24 and distributed by the multiplexer 60 between the multiple transducers 51, 52, 53. Therefore, the pulse repetition rate for each individual transducer 51, 52, 53 will be lower and can be calculated by dividing the pulse repetition rate of the signal generator by the number of transducers. A lower pulse repetition rate will result in either a lower scan resolution or lower scanning speed.

BRIEF DESCRIPTION OF THE DRAWINGS

Various examples objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1A:
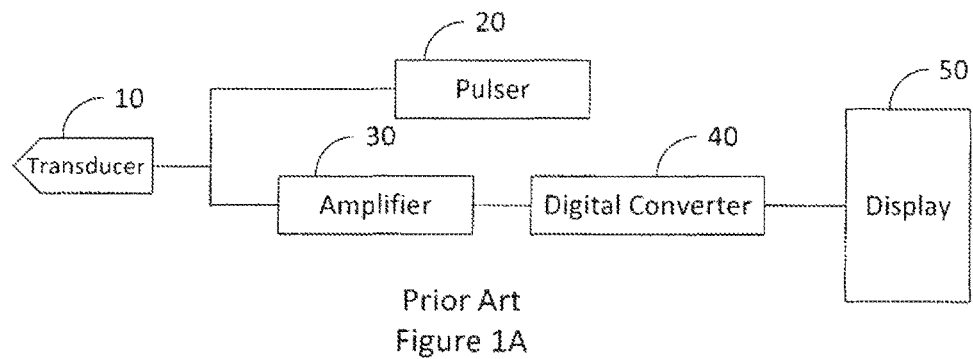
FIG. 1A is a block diagram showing a portion of a prior art scanning acoustic microscope having a single transducer with a single channel electronics configuration.
Figure 1B:
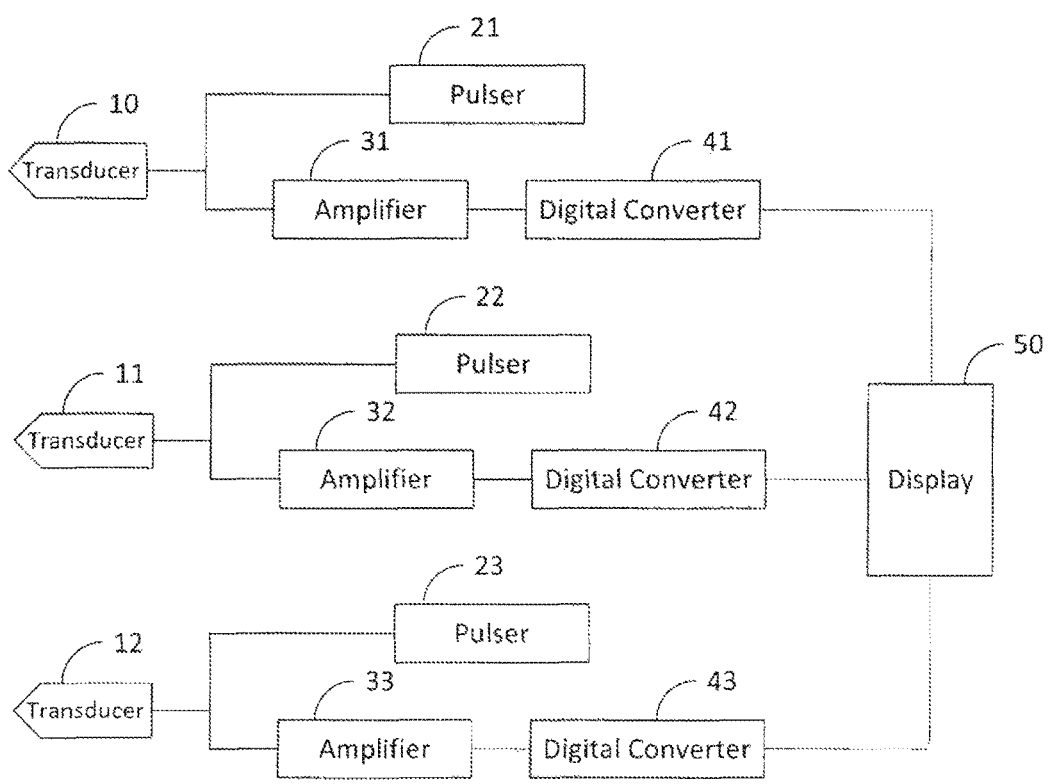
FIG. 1B is a block diagram showing a portion of a prior art scanning acoustic microscope having multiple transducers and a multi-channel configuration.
Figure 1C:
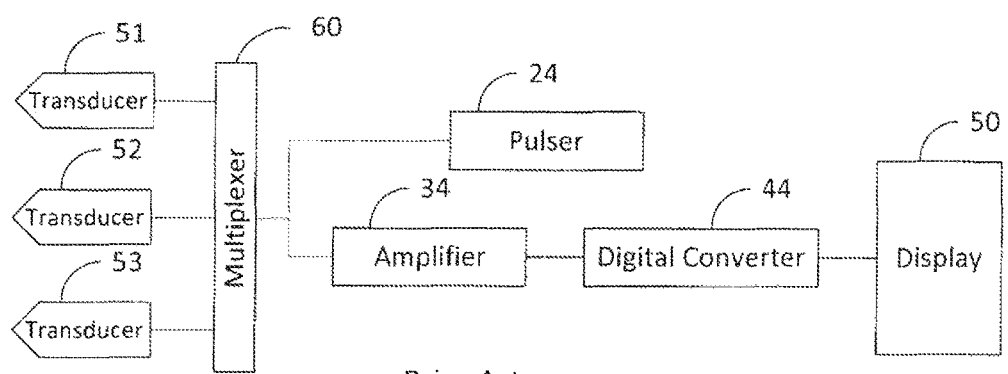
FIG. 1C is a block diagram showing a portion of a prior art scanning acoustic microscope having multiple transducers and single channel electronics configuration with multiplexing.
Figure 2:
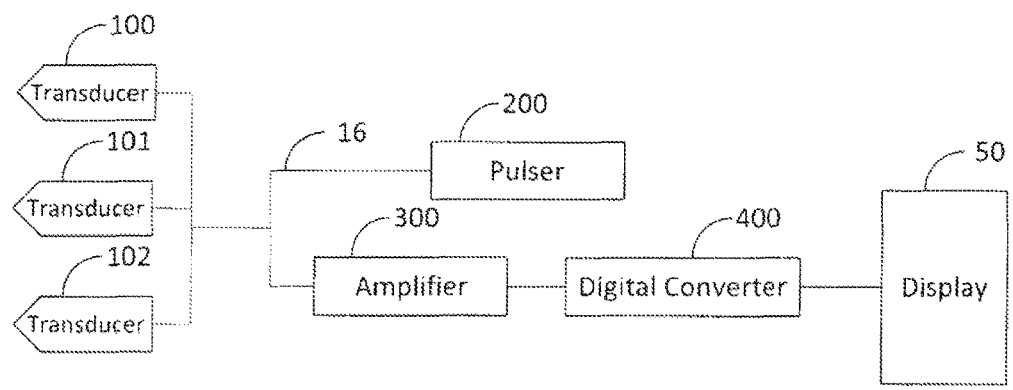
FIG. 2 is a block diagram showing a portion of a single channel scanning acoustic microscope with multiple transducers that forms an embodiment in accordance with the principles of the present disclosure.

The purpose of this invention is to increase the throughput of the acoustic imaging system by connecting a multi-transducer assembly 15 "in parallel" to a single channel electronic circuit 16 as, for example, shown in FIG. 2. The multi-transducer assembly 15 comprises transducers 100-102 and the single channel electronic circuit 16 comprises a transducer 10, a pulser 200, an amplifier 300, a digital converter 400 and a visual display, such as a monitor 50. This configuration has numerous advantages when compared with the prior art connections described in FIGS. 1A, 1B and 1C, The single channel electronic system 16, without multiplexing, does not reduce the pulse repletion rate and, as a result, will not lower the scan resolution or scanning speed. On the other hand, this system has a substantially lower cost when compared with the multi-channel systems since it requires a single electronic channel.

Figure 3:
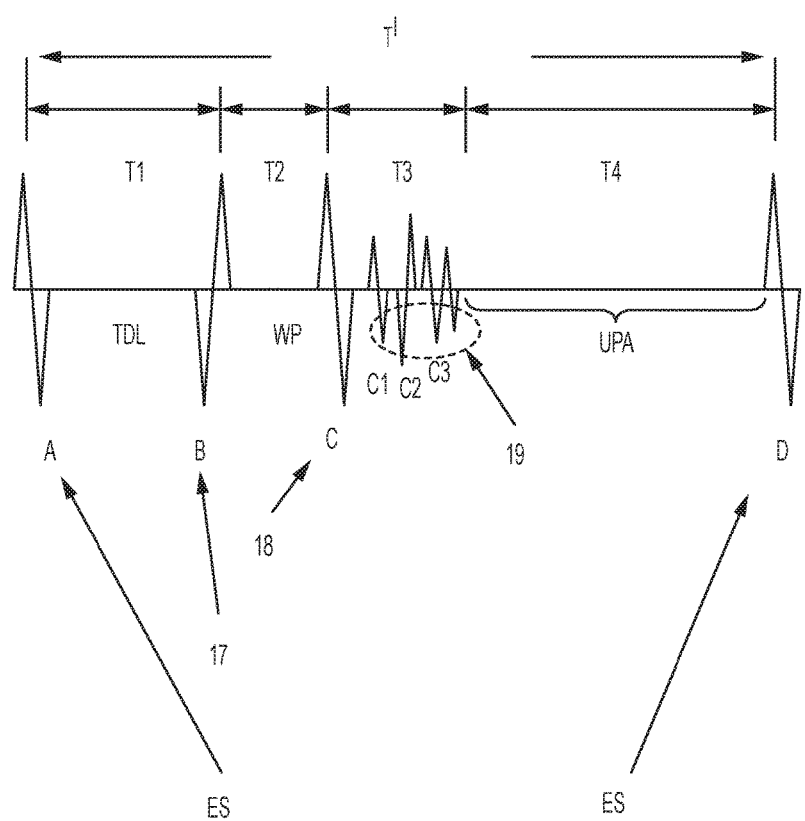
FIG. 3 is a graph showing an A-scan taken by one of the transducers shown in FIGS. 1A-C.
Figure 4:
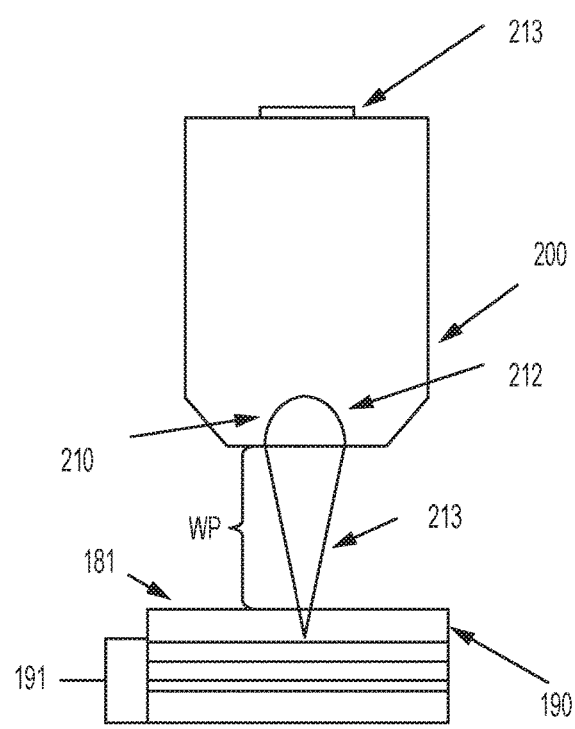
FIG. 4 is a side view of one of the transducers shown in FIG. 2 which emits a focused ultrasonic beam towards a part under inspection in accordance with the principles of the present disclosure.

In order to display and process the ultrasonic signals from multiple transducers 100-102 on the same A-scan waveform, proper time delays TDL for each individual signal should be introduced. A-scan waveform for a single focused ultrasonic transducer is shown in FIG. 3. The A-scan waveform usually displays multiple reflections of the ultrasonic waves that travel inside the ultrasonic transducer 100-102, down fluid or water path WP in between the ultrasonic transducer 100-102, onto the inspected part 190 as well as inside the inspected part 190. As shown in FIG. 4, a transducer 10 generates a focused ultrasonic beam 214 comprising a piezoelectric 213, an acoustic rod 200 and a lens 210 including a lens water interface 212. Said focused ultrasonic beam 213 travels inside the part for inspected part 190, wherein said focused ultrasonic beam 214 pass through a water-part interface 181 before reaching the inspected part 190. Reflections of the ultrasonic waves occur at the boundaries of materials with different acoustic impedances. All of the reflections from the material boundaries (i.e. part interior interfaces 191) are received by the same ultrasonic transducer 100-102, amplified, converted into digital format and then presented as a train of the high-frequency pulses.

Figure 5:
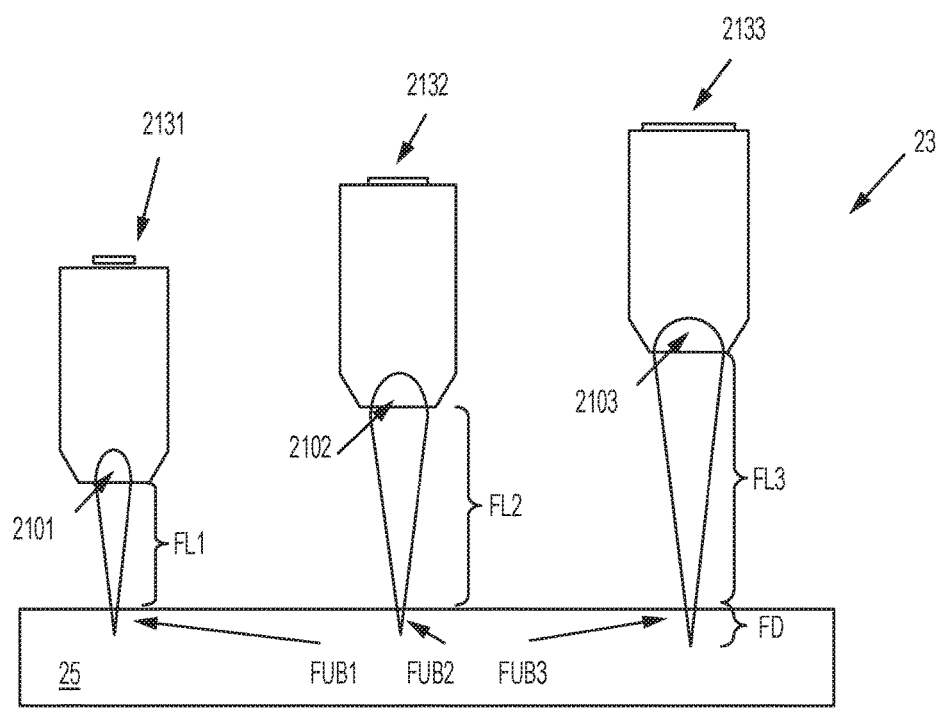
FIG. 5 is a side view of an embodiment in which three transducers emit focused ultrasonic beams at a single part under inspection in accordance with the principles of the present disclosure.

FIG. 3 shows ultrasonic signals, generated from the electric signal ES from the pulse generator 200 to activate piezoelectric 213, that are reflected from acoustic rod-water interface 17, with an approximately first time interval T1 of 5-19 μsec, a water-part interface 18 with an approximately second time interval T2 of 5-12 μsec and an interior interfaces 19 with an approximately third time interval T3 of 1-2 μsec inside the inspected part 190. The length of the acoustically transparent rod 200 with the lens 210, as shown in FIG. 4, varies based on the transducer design. In turn, the lens-part water path 212, as shown in FIG. 5, depends on the required focal depth FD inside the inspected part 190. However, for the majority of transducers and part configurations the round-trip times C1, C2, C3 of the signals of interest (signals reflected from the interior part interfaces 191) are substantially less than the total time interval $T^1$ of the A-scan which, in the FIG. 3 embodiment, is between 7-49 μsec T4 of downtime during which no data is being generated.

The "unused" portion of the A-scan can be utilized in a manner to allow the throughput of the scanning acoustic microscope to be greatly increased. One way to do this is to display the signals from multiple ultrasonic transducers 100-102 that are connected to the same single channel electronic system 16. For proper signal display and analysis, different time delays should be introduced for each transducer in the multi-transducer assembly. The time delays will prevent interference between individual signals and make independent "time-gating" possible using a single channel data acquisition system 16. The same single data acquisition channel can be used for the signal analysis and imaging.

The required time delays can be introduced using, for example, acoustic signal delays or electronic signal delays. Acoustic signal delays can be achieved using a water path delays configuration 23 as, for example, shown in FIG. 5 or a transducer rod delays configuration 24 as, for example, shown in FIG. 8.

Different water path WP delays can be achieved when transducers in the assembly are positioned at different distances from the top surface of the inspected parts 25 while each piezoelectric 2131, 2132, 2133 receives the electric signal ES simultaneously. The time delay selection is based on, for example, the number of transducers in the assembly (number of concurrent inspection areas), the material and configuration of the inspected parts as well as the required sensitivity, axial resolution and other parameters of the inspection procedure. The water path time delays subsequently affect selection of the individual transducers in the assembly. All transducer parameters including focal lengths FL1, FL2, FL3, lens 211, 2102, 2103 and piezoelectric crystal 2131, 2132, 2133 dimensions should satisfy the required inspection resolution.

Figure 6:
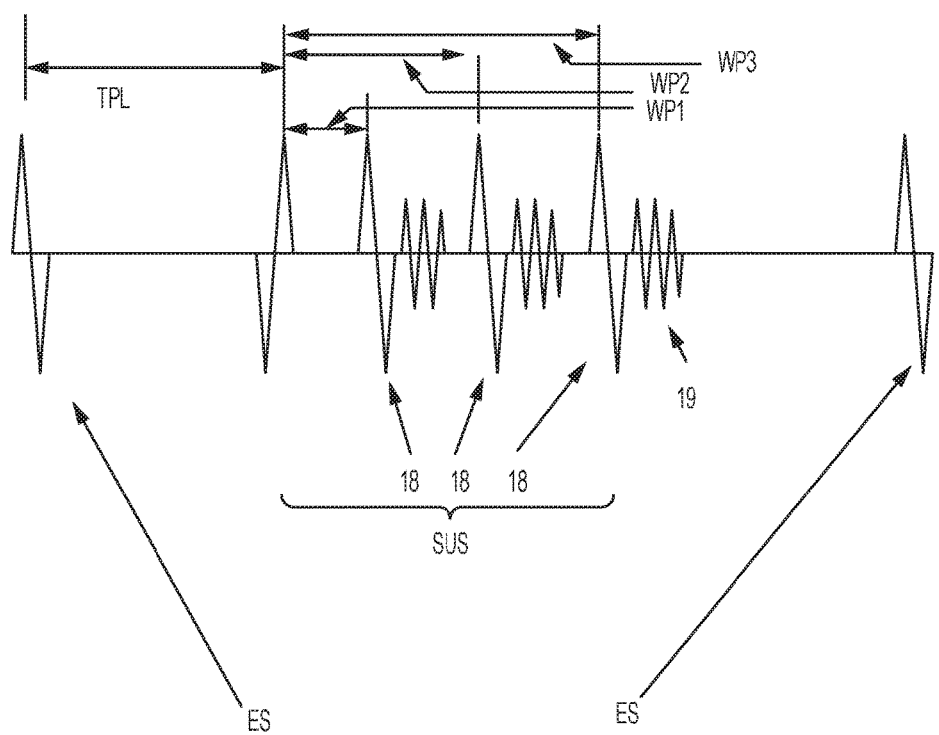
FIG. 6 is a graph showing an A-scan of the ultrasonic waveforms obtained when the FIG. 5 embodiment is used in accordance with the principles of the present disclosure.

FIG. 6 shows an A-scan waveform of the 3-transducer assembly 25 with water path delays WP1, WP2, WP3 as well as the time delays associated with the rods shown in FIG. 5. As shown in FIG. 6, the reflected ultrasonic signals from the lens-water interfaces are superimposed SUS (rod length is the same) while the water path delays WP1, WP2, WP3 introduce necessary time shifts. However, a focused ultrasonic transducer can be made without any delay line (rod) TDL. For example, some of the focused transducers have superimposed lenses and crystals when the piezoelectric materials are deposited directly on the lenses.

Figure 7:
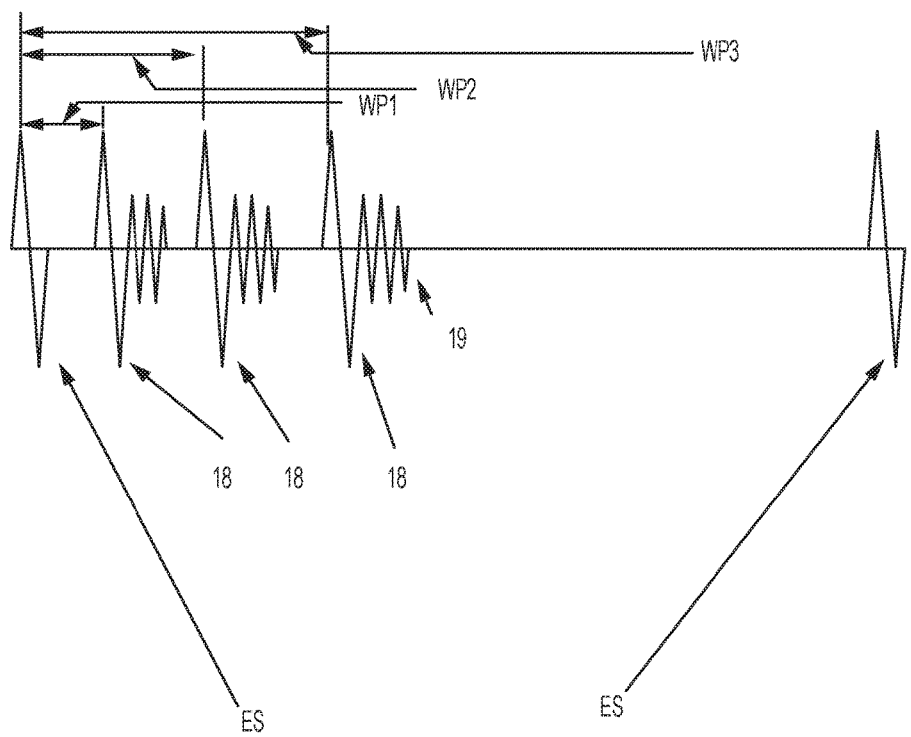
FIG. 7 is a graph showing an A-scan of the ultrasonic waveforms that would be obtained if the three transducers shown in FIG. 5 were replaced with transducers in which the piezoelectric crystals are attached directly to the lens in accordance with the principles of the present disclosure.

FIG. 7 is a graph showing water path delays WP1, WP2, WP3 configuration for the group of the transducers without acoustic rod 200. In this example, the piezoelectric crystal 213 is mounted directly on an ultrasonic lens 210. Without the delay associated with the rods TDL, and as shown in FIG. 7, all ultrasonic signals 18 are shifted to the left leaving more space for the signals from additional transducers in the group which gives the designer even more flexibility to increase throughput. For example, three transducers without rods can be used in addition to three other transducers that do, in fact, have rods. The presence of the extra rods gives extra delay time to separate the additional three signals from the signals generated by the transducers without rods.

Figure 8:
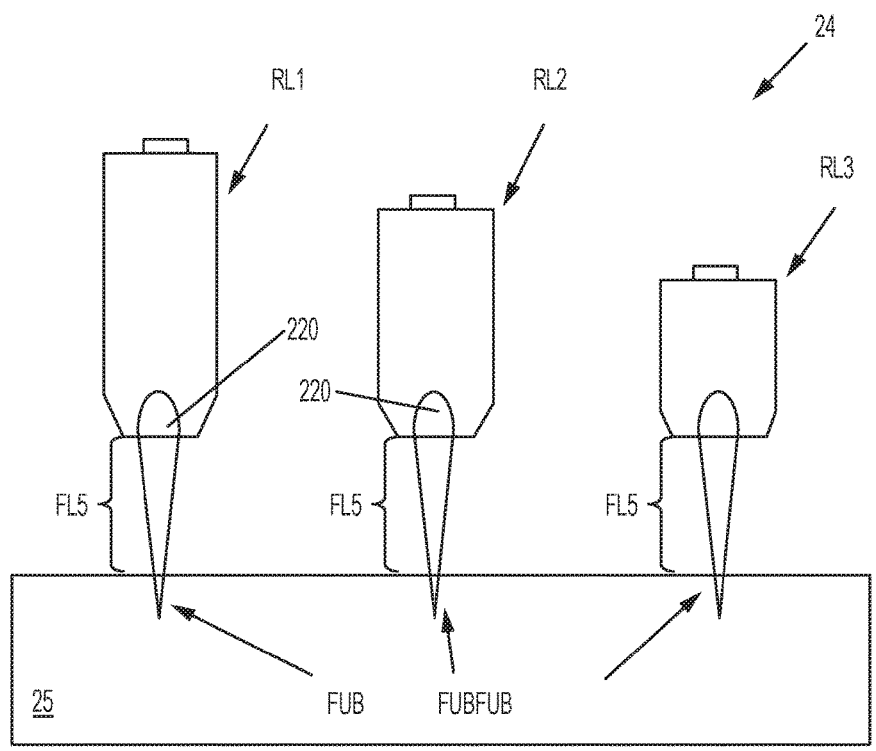
FIG. 8 is a side view of a second embodiment of the present invention in which three transducers emit focused ultrasonic beams at a single part under inspection in accordance with the principles of the present disclosure.
Figure 9:
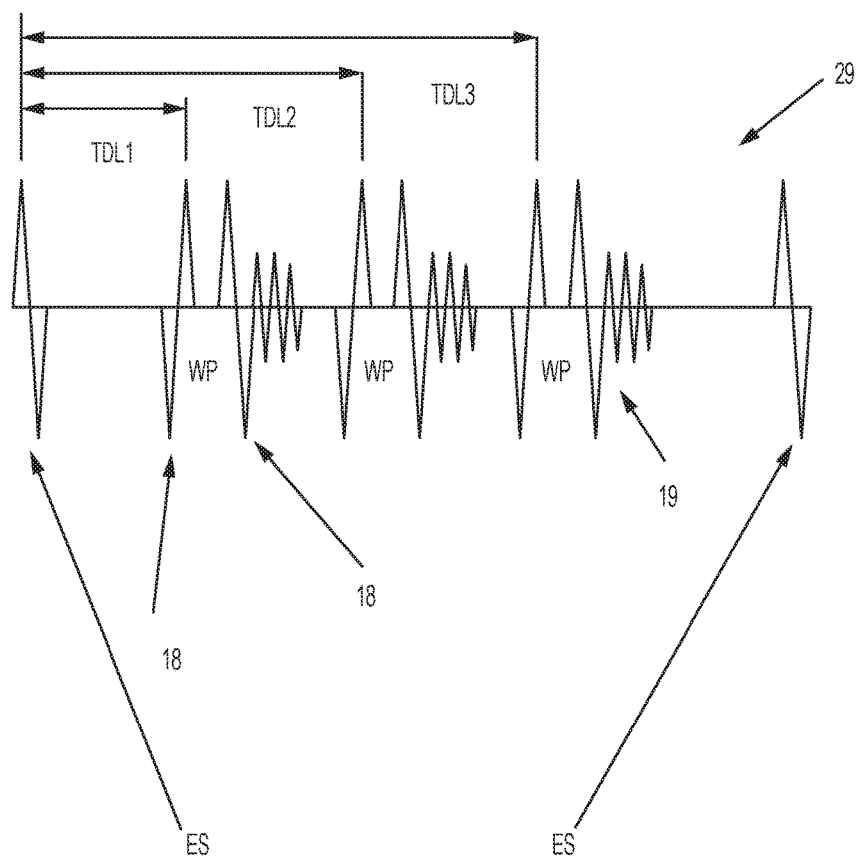
FIG. 9 is a graph showing an A-scan of the ultrasonic waveforms obtained when the FIG. 8 embodiment is used in accordance with the principles of the present disclosure.
Figure 10:
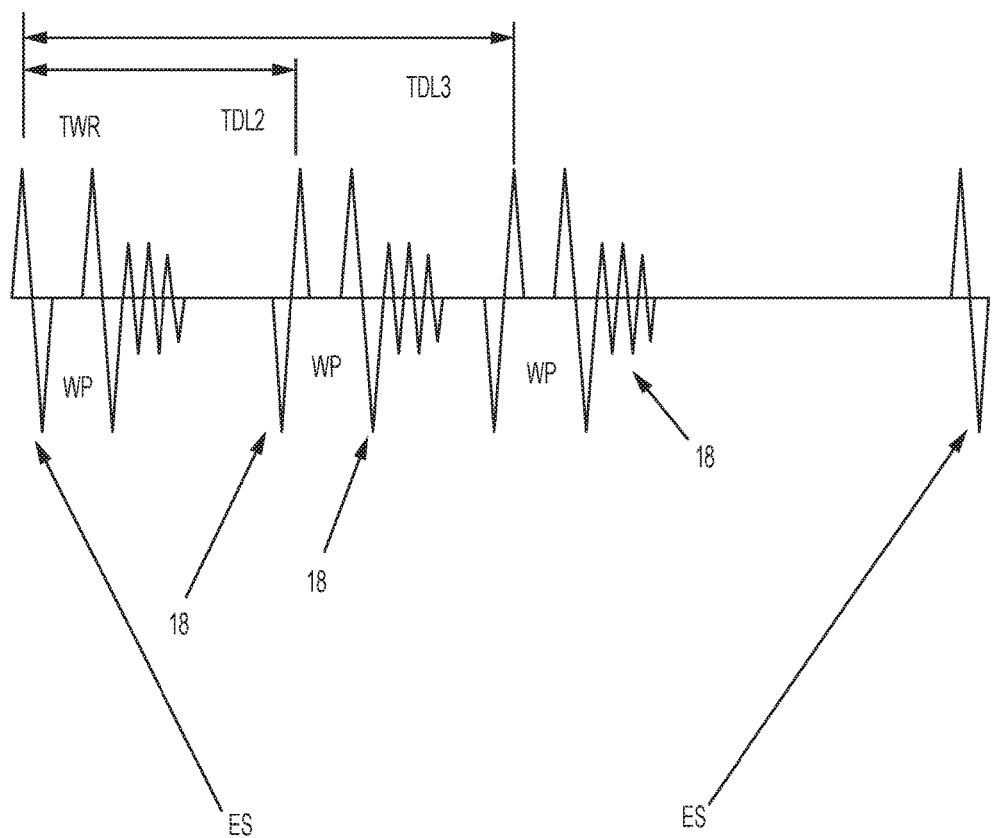
FIG. 10 is a graph showing an A-scan of the ultrasonic waveforms that would be obtained if one of the three transducers shown in FIG. 8 were replaced with piezoelectric crystals that are directly attached to a lens in accordance with the principles of the present disclosure.

Transducer rod delays of different lengths of time 24 are introduced by the different lengths of the acoustic rods RL1, RL2, RL3 as shown in FIG. 8. The transducers in the assembly are positioned at the same distance FL5 from the inspected part 25 and have similar lenses 220 and focal depths FD. FIG. 9 is a graph 29 that shows different time delays TDL1, TDL2, TDL3 for the signals from the lens-water interfaces while water path delays WP are equal for all three transducers shown in FIG. 8. At least one of the transducers in the group can, for example, have no rod. FIG. 10 shows A-scan waveform 30 with one of the transducers not having a rod and, therefore, no time delay TWR associated with the rod.

Electronic time delays can be introduced by commercially available delay lines or by a multi-channel pulse generator with proper delays in-between individual channels. With the multi-channel pulse generation ultrasonic signals are still analyzed and imaged by the single channel data acquisition system that makes the cost of the demonstrated system substantially lower than the cost of the multi-channel system.

Figure 11:
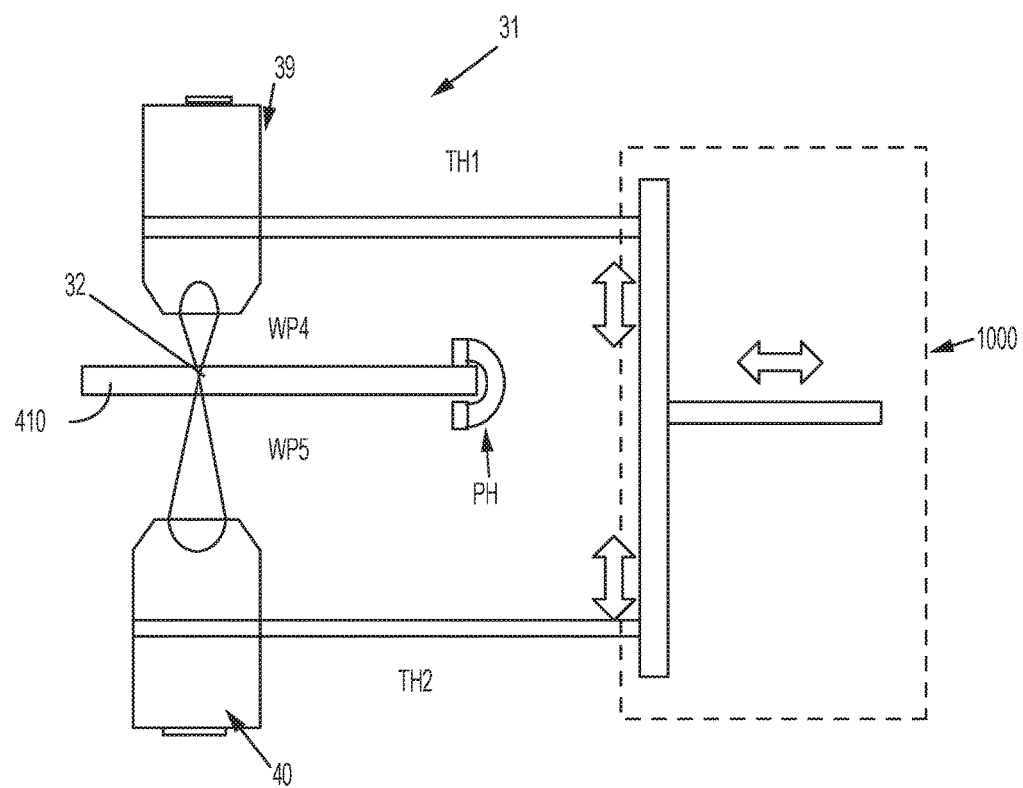
FIG. 11 is a particular embodiment of the present invention in which two transducers are used to simultaneously inspect both sides of a part in accordance with the principles of the present disclosure.
Figure 13:
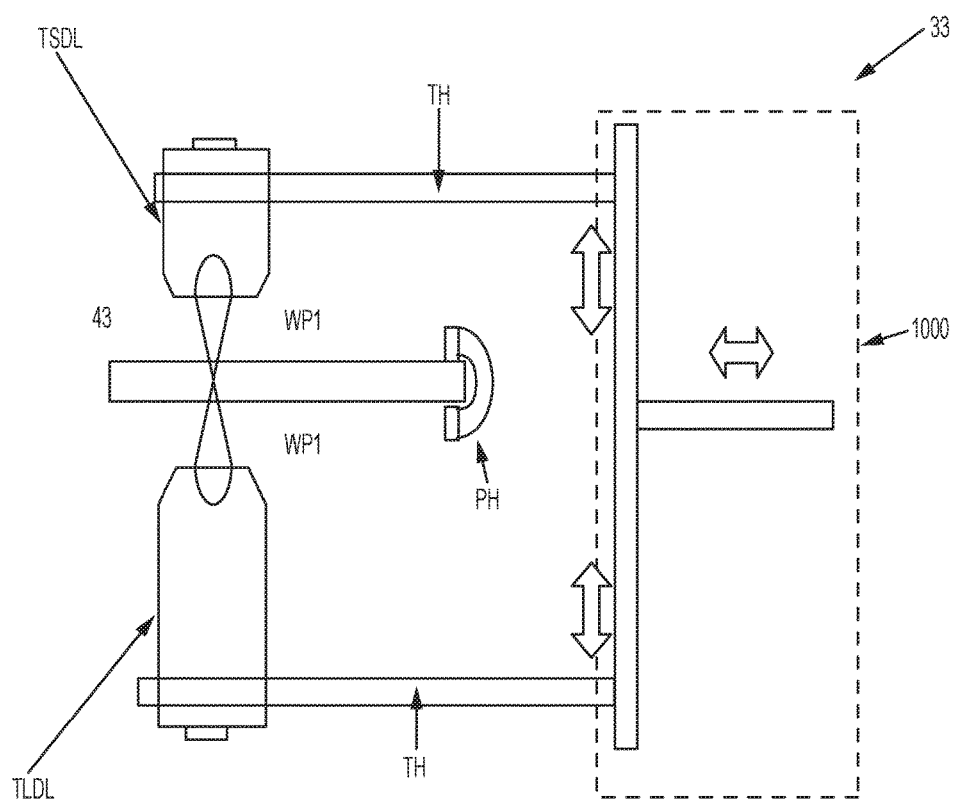
FIG. 13 is an alternative embodiment of the device shown in FIG. 11 in accordance with the principles of the present disclosure.

Transducers with water path delays or acoustic rod delays can be positioned on one or both sides of the inspected part as shown in FIG. 11 and FIG. 13. In the FIG. 11 embodiment, a dual-transducer assembly 31 with the water path time delays WP4, WP5 for the concurrent imaging 32 of the part from both sides is shown. A first transducer 39 is hold by a transducer holder TH1 and a second transducer 40 is hold by a transducer holder TH2. Both transducer holders TH1, TH2 are mechanically attached to a X-Y scanning system providing linear 1000 and rotational motion to said transducer holders TH1, TH2. The time delays in this embodiment are provided by, for example, spacing the transducers 39, 40 at different axial distances away from the part 410 to be inspected, wherein said part is held in position between transducers by means of a part holder PH.

In the FIG. 13 embodiment, a dual-transducer assembly with the acoustic rod time delays 33 for the concurrent imaging of the part from both sides is shown. The time delays in this embodiment are provided by, for example, the different length of the acoustic rods TSDL, TLDL.

Figure 12:
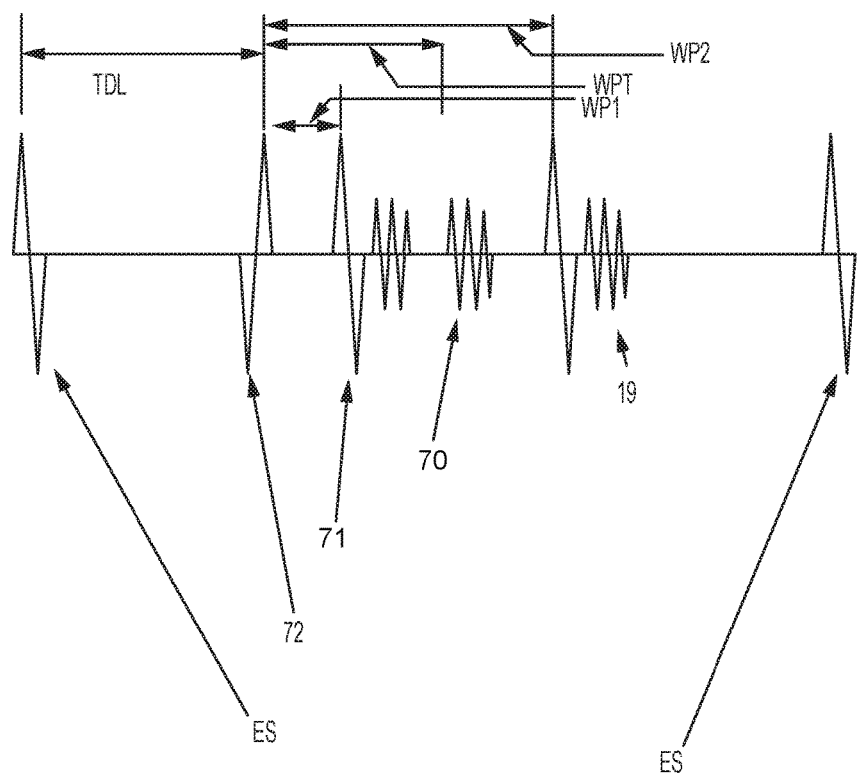
FIG. 12 is a graph showing an A-scan of the ultrasonic forms obtained when the FIG. 11 embodiment is used in accordance with the principles of the present disclosure.
Figure 14:
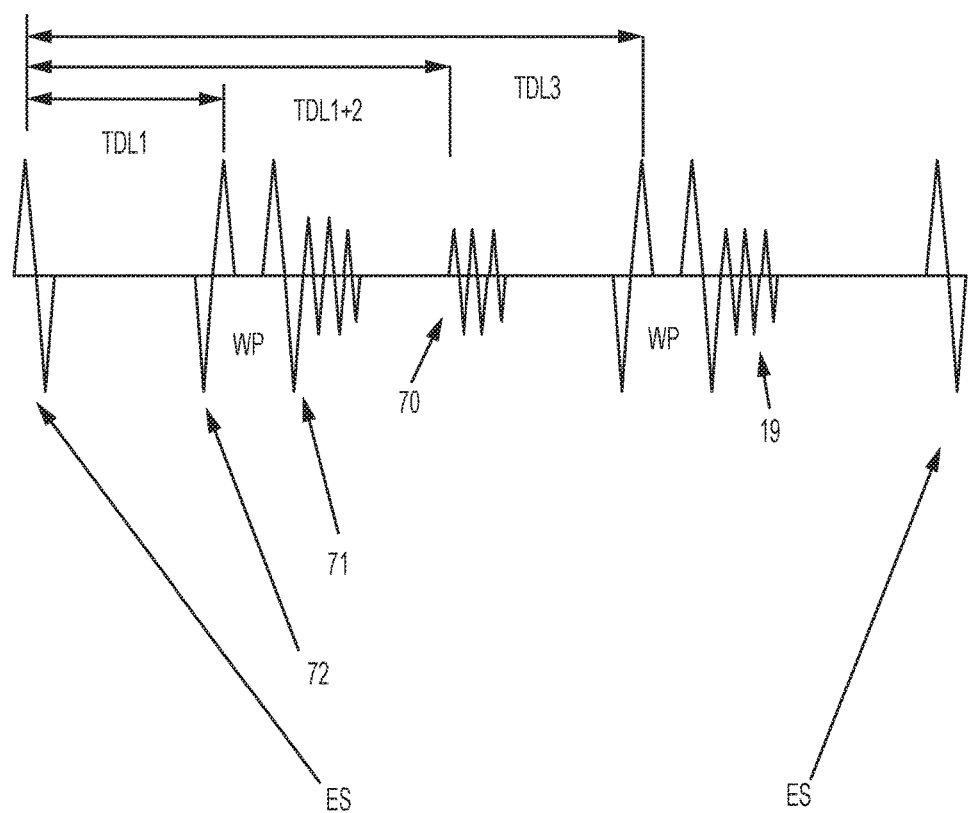
FIG. 14 is a graph showing an A-scan of the ultrasonic forms obtained when the FIG. 13 embodiment is used in accordance with the principles of the present disclosure.

The confocal configuration of the dual-transducer assembly makes it possible to acquire and simultaneously display several ultrasonic signals that are reflected from the inspected part 43 as well as transmitted through the part on the same A-scan waveform. The reflected and transmitted signals are shown in FIG. 12 for the dual-transducer assembly 31 configuration with the water path delays and in FIG. 14 for the dual-transducer assembly with the acoustic rod time delays 33. FIG. 14 shows different time delays TDL1, TDL1+2, TDL3 for the signals, wherein the TDL1 correspond to the delay for a first acoustic rod TSDL, TDL1+2 correspond to the delay difference between the first acoustic rod TSDL and a second acoustic rod TLDL and TDL3 correspond to the delay for second acoustic rod TLDL. After the electric signal ES from the pulse generator to activate the piezoelectric crystal is generated the first received signal is the ultrasonic signal reflected from the lens-water interface 72. Next is the ultrasonic signal reflected from water part interface 71 and further the ultrasonic signal transmitted 70 through the inspected part 43. Subsequent is the ultrasonic signals from the part interior interface 19. Reflected ultrasonic signals have higher amplitudes in areas with material irregularities while transmitted signal are diminished in the same areas. On the other hand flawless materials do not produce high amplitude reflected signals while creating low loss conditions for the transmitted signals. Therefore, the combination of the reflected and transmitted signals that can be presented as R/T ratios will substantially increase the contrast of the acoustic images and ultimately the probability of the detection.

Figure 15:
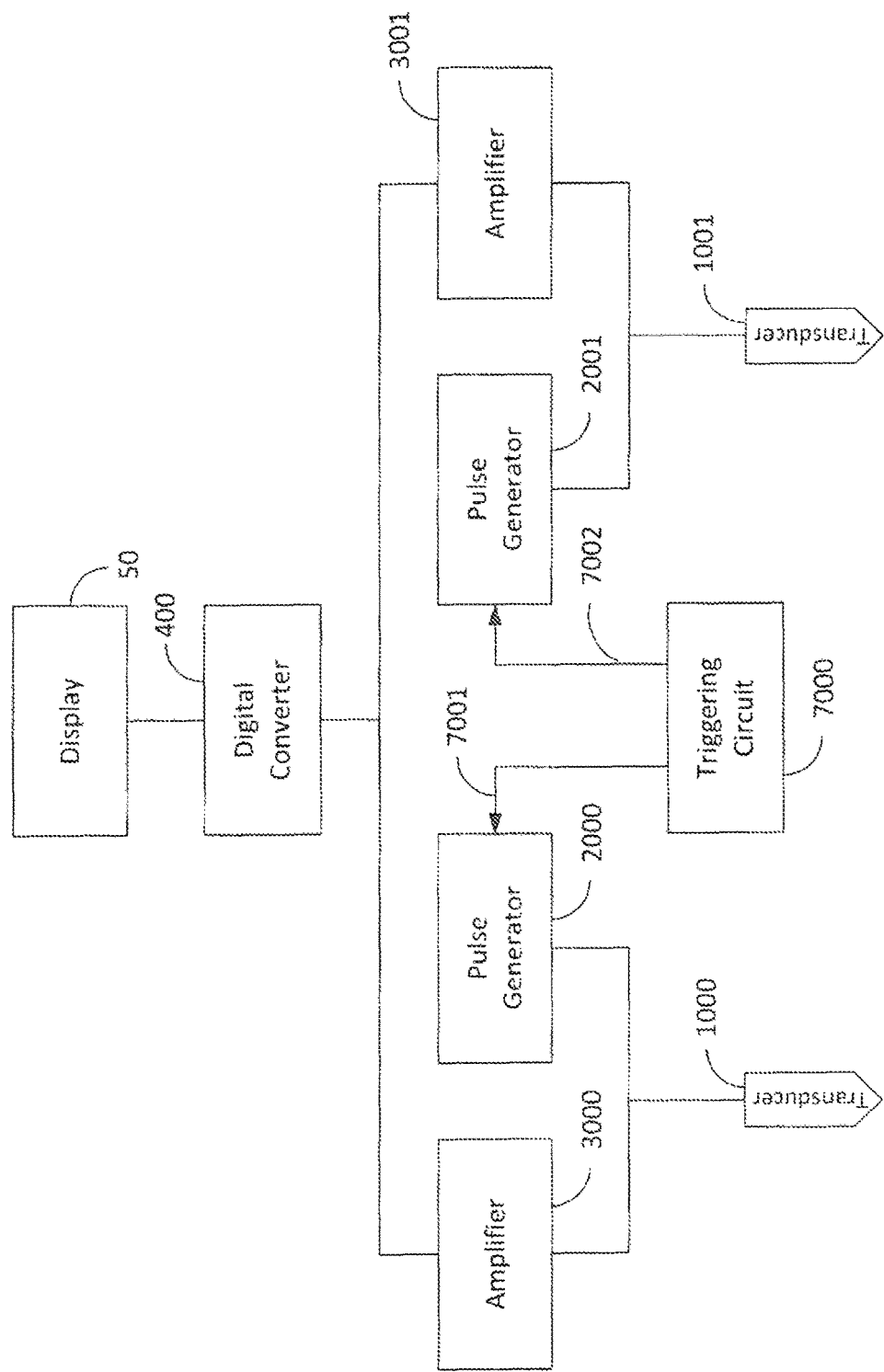
FIG. 15 is a block diagram of the dual-transducer/dual-pulser configuration in accordance with the principles of the present disclosure.

Further a dual transducer/dual-pulser with delay configuration is presented in accordance with the principles of the present invention, as shown in FIG. 15. In this example, time delay between transducers 1000, 1001 is introduced not by acoustical rod delay but by the electronic delay in the second pulse generator 2001. The delay can be precisely controlled by the commercially available triggering circuit 7000 comprising a not delay trigger 7001 and a delayed trigger 7002. This circuit provides fully programmable triggering sequences with wide range of time delays.

While the dual transducer/dual-pulser with delay configuration already requires at least two pulsers 2000, 2001 and two amplifiers 3000, 3001, all ultrasonic signals are still analyzed and imaged by the single channel data acquisition system, such as a digital converter 4000 and a visual display 50, that makes the cost of the demonstrated system substantially lower than the dual channel data acquisition system.

Figure 16:
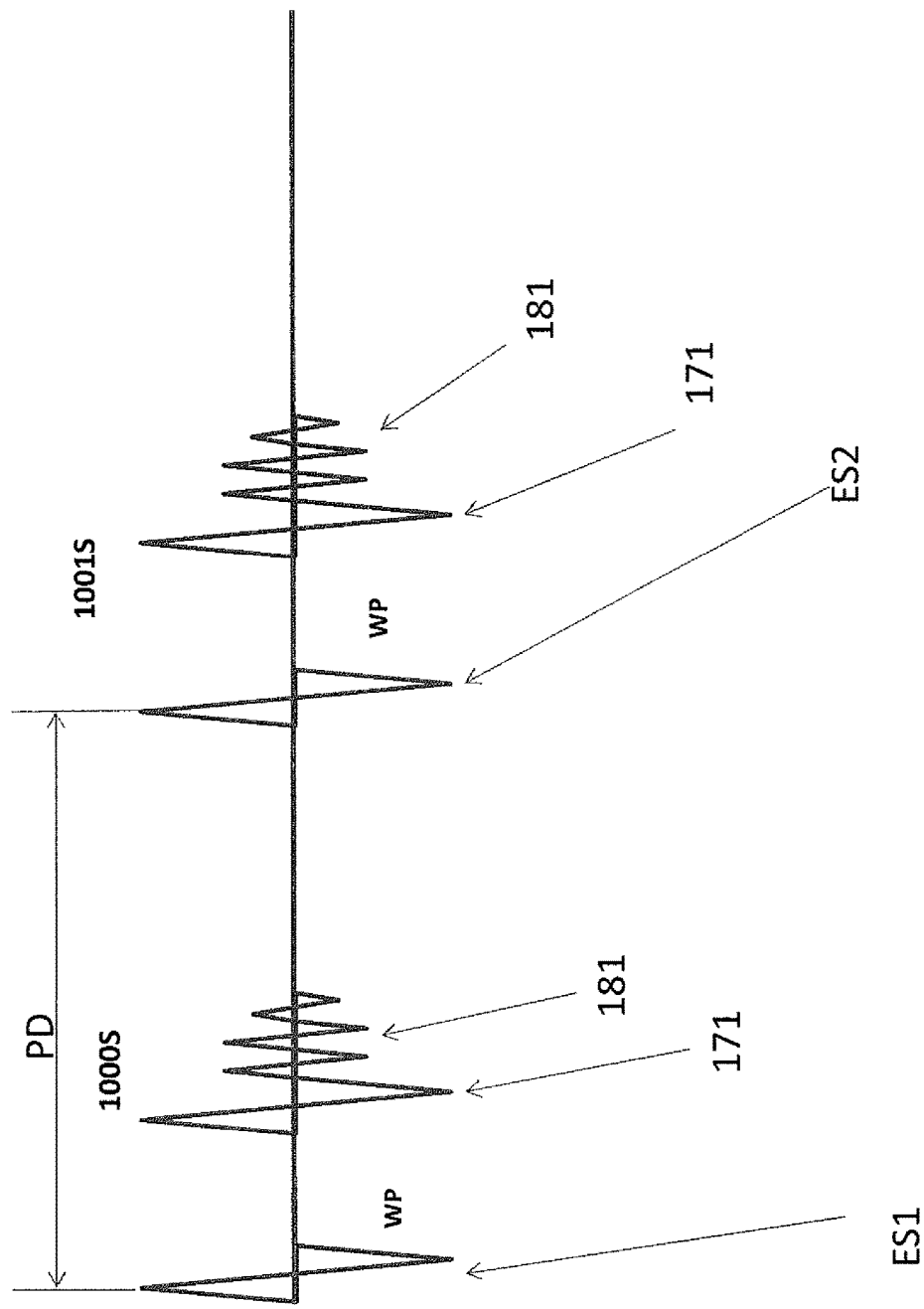
FIG. 16 is a graph showing an A-scan of the ultrasonic forms obtained when the FIG. 15 embodiment is used without rods in accordance with the principles of the present disclosure.

FIG. 16 shows A-scan waveform for dual-transducer/dual-pulser configuration of FIG. 15 for the ultrasonic transducers 1000, 1001 without acoustical delay rods. In this example, minimum time delay PD between generated pulses, wherein electrical signals from the first pulse generator ES1 activate a first transducer 1000 and wherein electrical signals from the second pulse generator ES2 activate a second transducer 1001, should be longer than the total roundtrip time required for the ultrasonic waves to travel through the transducer-specimen water path 171 and the thickness of the specimen 181. On the other hand, maximum time delay should be shorter than the pulse repetition interval (PRI) of the pulse generator (approximately 40-60 μsec).

The proper pulse delay PD for the transducers 1000, 1001 without rods can be expressed as follows:

$$2\Delta T\text{waterpath} + 2\Delta T\text{specimen} < \Delta T\text{pulse} < \Delta T\text{PRI}$$

Figure 17:
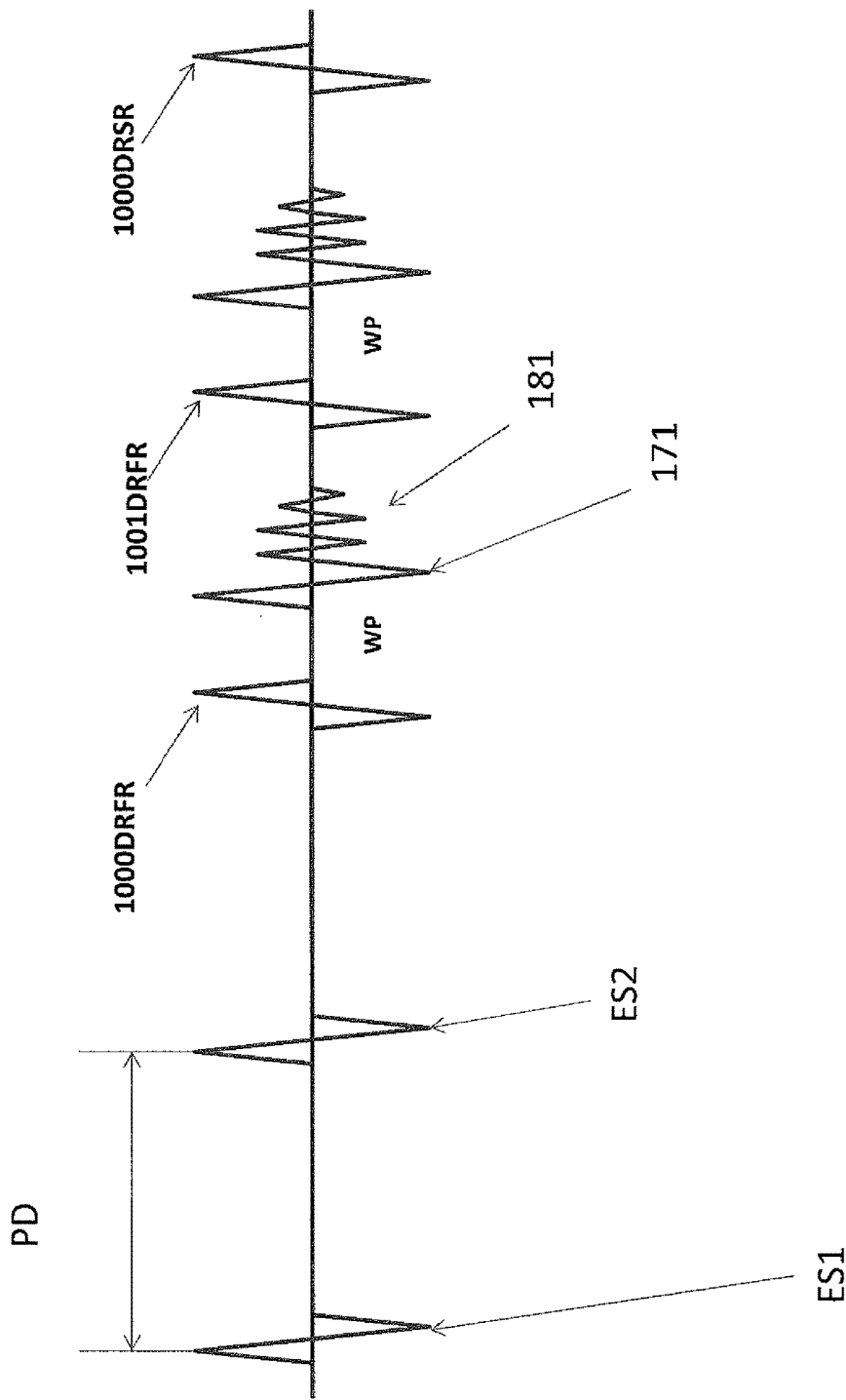
FIG. 17 is a graph showing an A-scan of the ultrasonic forms obtained when the FIG. 15 embodiment is used with rods in accordance with the principles of the present disclosure.

There are some types of the ultrasonic transducers 1000, 1001 that cannot be manufactured without acoustical delay rods. FIG. 17 shows A-scan waveform for dual-transducer/dual-pulser configuration for the ultrasonic transducers

1000, 1001 with acoustical delay rods. Acoustical delay rods usually produce multiple reflections for example a first transducer delay first reflection 1000DRFR, a second transducer delay first reflection 1001DRFR and a first transducer delay second reflection 1000DRSR from the rod/water path interface 171 resulting in the high-amplitude signals on the A-scan waveforms. These signals are equally spaced by the time interval based on the length and material of the delay rod. Interference of the specimen 181 and delay rod signals can substantially distort acquired ultrasonic images. Therefore, proper imaging procedure assumes positioning of the specimen signals in-between subsequent acoustical rod reflections.

In the case of the dual-transducer/dual-pulser system proper pulse generator delay should be selected to prevent cross-interference between first and second transducers' "signal trains".

Assume that two identical transducers are used. Also assume that we use the time window in-between first 1000DRFR and second 1000DRSR delay rod reflections of the transducer with no-delay pulser.

In this example, minimum pulse delay should be longer than the total roundtrip time required for ultrasonic waves to travel through the transducer-specimen water path 171 and the thickness of the specimen 181. On the other hand, maximum pulse delay PD should be shorter than the two roundtrip times in the delay rod minus the total time required for ultrasonic waves to travel through the transducer-specimen water path 171 and the thickness of the specimen 181.

The proper pulse delay for the transducers with rods can be expressed as follows:

$$2\Delta T\text{waterpath} + 2\Delta T\text{specimen} < \Delta T\text{pulse} < 4\Delta T\text{rod} - 2\Delta T\text{waterpath} - 2\Delta T\text{specimen}$$

U.S. Pat. Nos. 9,170,236; 8,794,072; 8,720,273; 7,584,664; 7,522,780; 7,395,713; 7,000,475; 6,981,417; 6,895,820; 6,890,302; 6,880,387; 6,460,414; 6,357,136; 5,684,252; 5,600,068; 4,866,986; 4,781,067 and 4,518,992, all relate to various aspects of scanning acoustic microscopy and all are currently owned by Sonoscan, Inc. The contents of all of these patents, publications and pending applications are incorporated by reference into this application as if fully set forth herein. It is within the scope of the present invention disclosed herein to utilize any of the techniques disclosed in any of the above-noted patents, published applications and pending application in connection with anyone or more aspects of the present invention.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A scanning acoustic microscope for scanning a part under inspection, the scanning acoustic microscope comprising:

a single channel electronic circuit configuration comprising a pulse generator, an amplifier, and a digital format converter; and a plurality of transducers, wherein each transducer comprises an acoustic rod body, at least one piezoelectric crystal, and at least one lens, wherein each transducer is configured to generate an ultrasonic wave, wherein said ultrasonic wave generated by each transducer has a different time delay relative to ultrasonic waves generated by other transducers prior to reaching the part under inspection, wherein each transducer is connected to said single channel electronic circuit configuration, and wherein each transducer is continuously electrically coupled to the digital format converter.

2. The scanning acoustic microscope of claim 1, wherein:
a fluid at least covers the distance between said plurality of transducers and said part under inspection,
the fluid located between each transducer and said part under inspection generates an individual fluid path for each transducer, and
said individual fluid path for each transducer results in an acoustic signal delay for each ultrasonic wave.

3. The scanning acoustic microscope of claim 2, wherein said acoustic signal delay is generated based on different lengths for each individual fluid path.

4. The scanning acoustic microscope of claim 3, wherein the ultrasonic wave generated by each transducer travels onto the part under inspection.

5. The scanning acoustic microscope of claim 1, wherein:
a fluid at least covers the distance between said plurality of transducers and said part under inspection,
the fluid located between said plurality of transducers and said part under inspection generates an individual fluid path, and
said acoustic rod body comprises a rod length, wherein the rod length for each transducer results in an acoustic signal delay for the ultrasonic wave.

6. The scanning acoustic microscope of claim 5, wherein the rod length for each transducer is different.

7. The scanning acoustic microscope of claim 5, wherein each ultrasonic wave travels onto the part under inspection.

8. The scanning acoustic microscope of claim 1, wherein said at least one piezoelectric crystal is directly attached to a first end of the acoustic rod body and said lens is connected to a second end of the acoustic rod body.

9. The scanning acoustic microscope of claim 1, wherein the time delay is introduced using an electronic signal delay applied to at least one of the transducers.

10. The scanning acoustic microscope of claim 1, wherein the single channel electronic circuit configuration further comprises a visual display.

11. The scanning acoustic microscope of claim 1, wherein transducers in a first group of transducers selected from the plurality of transducers are each positioned at different distances from a top side of the part under inspection resulting in the time delay for each transducer.

12. The scanning acoustic microscope of claim 1, wherein signal delays for the ultrasonic waves generated by the plurality of transducers are based on different acoustic rod lengths for each of the plurality of transducers.

13. The scanning acoustic microscope of claim 1, wherein signal delays for the ultrasonic waves generated by the plurality of transducers are based on different lengths of individual fluid paths between said plurality of transducers and said part under inspection.

14. The scanning acoustic microscope of claim 1, wherein each of the plurality of transducers generates the ultrasonic wave and receives a reflection of the ultrasonic wave off the part under inspection.

15. A scanning acoustic microscope, comprising:
a plurality of transducers, wherein two or more of the transducers each emits a focused ultrasonic beam towards a part under inspection,
wherein each of the plurality of transducers comprises an acoustic rod, at least one lens at a second end of each transducer, and a piezoelectric crystal directly attached to the acoustic rod,
wherein a first end of each transducer is connected to a single channel electronic circuit, and
wherein a reflection of said ultrasonic beam that travels into the part under inspection from each transducer is received by the same transducer with a time delay, and a signal based on the received reflection of said ultrasonic beam is transmitted to the single channel electronic circuit.

16. The scanning acoustic microscope of claim 15, wherein the time delay is an acoustic time delay.

17. The scanning acoustic microscope of claim 16, wherein the plurality of transducers are each positioned at different distances from a top side of the part under inspection resulting in the acoustic time delay.

18. The scanning acoustic microscope of claim 14, wherein the acoustic rods have different lengths.

19. The scanning acoustic microscope of claim 15, wherein the time delay is introduced using an electronic signal delay.

20. The scanning acoustic microscope of claim 15, wherein said two or more transducers are positioned around the part under inspection to concurrently image said part under inspection.

21. The scanning acoustic microscope of claim 20, wherein the time delays result from spacing each transducer at different axial distances from the part to be inspected.

22. The scanning acoustic microscope of claim 20, wherein the time delays result from different lengths of the acoustic rods.

23. The scanning acoustic microscope of claim 15, wherein the time delays for the focused ultrasonic beam generated by the plurality of transducers are based on different lengths of individual fluid paths between said plurality of transducers and said part under inspection.

24. A scanning acoustic microscope, comprising:
a plurality of transducers including at least one transmitting transducer and at least one receiving transducer, the at least one transmitting transducer emitting a focused ultrasonic beam towards a part under inspection,
wherein each of the plurality of transducers comprises an acoustic rod, at least one lens at a second end of each transducer, and a piezoelectric crystal directly attached to the acoustic rod,
wherein a first end of each transducer is connected to a single channel electronic circuit,
wherein the focused ultrasonic beam is emitted from the transmitting transducer, travels into the part under inspection, and is received by the receiving transducer with a time delay, and
wherein a signal based on the received transmission of said ultrasonic beam through the part under inspection is transmitted to the single channel electronic circuit.

25. The scanning acoustic microscope of claim 24, wherein:
a fluid at least covers the distance between said plurality of transducers and said part under inspection,
the fluid located between each transducer and said part under inspection generates an individual fluid path for each transducer, and
said individual fluid path for each transducer results in an acoustic signal delay for each ultrasonic wave.

26. The scanning acoustic microscope of claim 25, wherein said acoustic signal delay is generated based on different lengths for each individual fluid path.

27. The scanning acoustic microscope of claim 24, wherein:
a fluid at least covers the distance between said plurality of transducers and said part under inspection,
the fluid located between said plurality of transducers and said part under inspection generates an individual fluid path, and
said acoustic rod comprises a rod length, wherein the rod length for each transducer results in an acoustic signal delay for the focused ultrasonic beam.

28. The scanning acoustic microscope of claim 27, wherein the rod length for each transducer is different.

29. The scanning acoustic microscope of claim 24, wherein the at least one transmitting transducer is positioned on a top side of the part under inspection, and the at least one receiving transducer is positioned on a bottom side of the part under inspection.

30. The scanning acoustic microscope of claim 24, wherein time delays for the focused ultrasonic beam generated by the plurality of transducers are based on different acoustic rod lengths for each of the plurality of transducers.

31. The scanning acoustic microscope of claim 24, wherein time delays for the focused ultrasonic beam generated by the plurality of transducers are based on different electronic signal delays applied to the plurality of transducers.

32. The scanning acoustic microscope of claim 24, wherein time delays for the focused ultrasonic beam generated by the plurality of transducers are based on different lengths of individual fluid paths between said plurality of transducers and said part under inspection.

* * * * *